United States Patent [19]
Petteruti

[11] 4,356,179

[45] Oct. 26, 1982

[54] FORMALDEHYDE PRODUCTS AS AGRICULTURAL FUNGICIDES

[76] Inventor: Alfredo Petteruti, Via Garibaldi 35, Sessa Aurunca (Caserta), Italy

[21] Appl. No.: 96,185

[22] Filed: Nov. 20, 1979

[30] Foreign Application Priority Data

Nov. 22, 1978 [IT] Italy .................................. 6405 A/78
May 29, 1979 [IT] Italy ............................... 40431 A/79

[51] Int. Cl.³ ..................... A01N 31/14; A01N 35/02; A01N 43/64; A01N 47/28
[52] U.S. Cl. .................................. 424/249; 424/322; 424/334; 424/342
[58] Field of Search ................. 424/82, 334, 249, 322, 424/342

[56] References Cited

U.S. PATENT DOCUMENTS

| | | | |
|---|---|---|---|
| 1,785,641 | 12/1930 | Melhus .................................. | 424/82 |
| 2,425,677 | 8/1947 | Hinegardner et al. ............... | 424/334 |
| 2,536,983 | 1/1951 | Owen .................................... | 424/82 |
| 2,692,252 | 10/1954 | Falck ..................................... | 424/82 |
| 2,730,554 | 1/1956 | Schetty et al. ...................... | 424/334 |
| 2,786,081 | 3/1957 | Kress .................................... | 424/334 |
| 3,223,513 | 12/1965 | Geary .................................... | 424/82 |
| 3,469,002 | 9/1969 | Moyer et al. ........................ | 424/334 |

OTHER PUBLICATIONS

Walker, J. Frederic, "Formaldehyde", 2nd Ed. ACS Monograph, Reinhold Publishing Corp. (1953) pp. 202–215, 235–259, 271–273, 281–283, 292–301, 306–309, 404–405 and 457–460.
The Merck Index, 9th Edition (1976) at p. 89.

*Primary Examiner*—Natalie Trousof
*Assistant Examiner*—L. Hendriksen
*Attorney, Agent, or Firm*—Martin Smolowitz

[57] ABSTRACT

Formaldehyde and reaction products thereof are applied to the bark or leaves of chestnut trees as well as those trees bearing stone fruits, e.g. peach, apricot, plum, cherry, etc., to prevent or cure fungus infections.

9 Claims, No Drawings

FORMALDEHYDE PRODUCTS AS AGRICULTURAL FUNGICIDES

The present invention concerns the use of formaldehyde, of the compounds and the polymers thereof as fungicides and bactericides in agriculture, for the prevention and/or the treatment of all those plants which may be threatened, or which are already attacked, by diseases of the stalk of the fungal or bacterial kind, particularly for the treatment of the gummosity of the Drupaceas and the cancer of the bark of the chestnut tree.

It is well known that many vegetals are subject to parasitic gummosity and to the cancer of the bark, which diseases are substantially due to mold or bacterial agents. Said diseases of the plants, if not duly prevented or cured in time, may cause a real murrain which, in some exceptional cases, can even lead to the extinction of the species.

The actual knowledge of vegetal pathology suggests the use of some preparations, but only for preventing and not for treating and, in any case, only limited to parasitic gummosity. Furthermore, no remedy is provided either for preventing and, particularly, or for the treatment of the cancer of the bark. Therefore, actually only for a restricted number of plants which are subjected to fungal or bacterial diseases a remedy is provided which, however, does not have any effect when the disease is rather advanced and has already attacked the inside of the tissues and, especially, of the bark. In some cases, the death of the plant can also be thus provoked.

It is therefore the aim of the present invention to realize preparations acting for the prevention and, most of all, for the cure, as fungicides or bactericides, of cancer of the bark, as well as like antidotes for other diseases of the stalk, and to suggest a process for the application of those preparations which does not cause damage to the further growing of the plants.

The present invention reaches the aim set forth by substantially using:

(1) free formaldehyde (HCHO) or combined with compounds, preferably having the following functional groups:
  (a) primary amino (—$NH_2$); secondary amino (—NH); tertiary amino (—N);
  (b) phenolic hydroxyl (—OH);
  (c) alcoholic hydroxyl, producing acetals or formals;
  (d) carboxylic and hydroxy (—COOH) and (—OH);
  (e) of the thioalcohols or thiophenols (—SH);
(2) or using products which add to the formaldehyde, like, for example:
  bisulphite $KHSO_3$
  ammonia $NH_3$, as hexamethylenetetramine [$(CH_2)_6N_4$];
(3) or using polymerization products of formaldehyde, such as:
  paraformaldehyde (polyoxymethylene) (—$CH_2O$)$_x$;
  trioxymethylene (—$CO_2O$—)$_3$;
(4) or using methyl ethers of the methylolureas and the methylolmelamines;
(5) or using the reaction or polymerization products of the compounds mentioned in points 1, 2, 3 and 4, with the same or with other different compounds;
(6) or using the above said compounds with or without the addition of buffer substances like citrates, tannic acid, etc., proceeding, according to the different cases and to the kind of intervention (prevention or cure), according to the stage of the disease and to the kind of the plant, to the application of said preparations:
  onto the bark: only onto the diseased areas, for a cure;
  onto the leaves: as a treatment; and/or
  onto the bark of the whole plant, once all the leaves have fallen, for prevention.

The main principle of the present invention consists in the recognition, similarly to medicine, that formaldehyde, due to the clear and exceptional fungicidal and bactericidal, and therefore curative features, can be used, especially as the compounds thereof, for the prevention and the cure of diseases of the plants caused by molds or bacteria. In fact, the compounds of formaldehyde partially retain the curing and preventing features, thus reducing the toxicity, and are well tolerated by the organisms.

Beyond the compounds of formaldehyde (HCHO) mentioned at points 2 and 6, the formaldehyde, when combined with the functional groups of point 1, produces, in the same order mentioned above, many compounds, some of which are listed hereinbelow, for exemplifying and not limitative purposes:

(a)
  monomethylolurea: $H_2NCONHCH_2OH$
  dimethylolurea: $HOCH_2HNCONHCH_2OH$
  monomethyleneurea: $H_2NOCON=CH_2$
  monomethylolthiurea: $H_2NCSNHCH_2OH$
  hexamethylolmelamine: $C_3N_6(CH_2OH)_6$ (b)
  hydroxydiphenylmethane: $(C_6H_4OH)_2CH_2$
  dimethylolphenol: $C_6H_3OH(CH_2OH)_2$
  monomethylolresorcinol: $C_6H_3(OH)_2CH_2OH$ (c) a reaction product between an alcohol, for example polyvinyl alcohol (—$CH_2CHOH$—)$_x$ and formaldehyde;

(d) anhydromethylenecitric acid: $(HOOCCH_2)_2C(OCOCH_2O)$ (e) mercaptals: $CH_2(SC_2H_5)_2$.

According to the present invention, the compounds with formaldehyde are eventually combined with buffer substances and, as already said, applied, according to the kind of use (for prevention or cure):

(A) directly onto the leaves, provoking a substantially curative action;

(B) onto the bark, onto the whole plant, once all the leaves have fallen, causing a substantially preventative action;

(C) onto the bark, in any season, and only onto the diseased areas, provoking a substantially preventative action.

All the substances and compounds hereinbelow described in detail, have been widely experimented with in the laboratory and also on some vegetals living in nature, particularly for the treatment of the parasitic gummosity of the Drupaceas (due to the "Coryneum Beijerinnckii" and other fungal agents), for the treatment of cancer of the bark of the chestnut tree (caused by Pirenomicete "Endothia parasitica"); but said substances can also be used in the case of other diseases of the stalk of fungal and bacterial kind, and on other vegetal species.

One of the reasons which, according to the present invention, have caused the experimentation and realizations of the compounds of the aldehyde for said purposes, is that the non-combined formaldehyde, just due to the reactivity and volatility thereof can not be directly applied onto the leaves, because said substance would burn the leaves, and would not be sufficiently absorbed. Therefore, the aldehyde has been transformed into soluble compounds which are solid and tolerated and which, once absorbed, are still in condition to perform a curative action in the vegetal organism, together with traces of non-combined formaldehyde. Said curing action is determined:
(1) by the presence of organic acids emitted by the diseased parts of the bark, whereby said acids act as catalyst which facilitate the formation of polymers (amino- and phenol-formaldehyde) being insoluble and unattackable, around the diseased parts, thus stopping the action of the pathogenic agent;
(2) by the balance action sufficiently directed towards the reagents, a phenomenon which provokes the direct contact with the freed formaldehyde;
(3) by the stimulus for the growing of antagonist molds.

The process according to the present invention, making use of the compounds before mentioned and which will be described in detail hereinbelow, has been tested for many years particularly for the treatment of the gummosity of the Drupaceas, due to parasitic molds (Coryneum, etc.) and to bacteria, as well as for the cure of cancer of the bark of the chestnut tree, caused by the "Endothia parasitica" mold, but can be used also in the case of other diseases of the stalk of a fungal or bacterial kind.

In the following some examples of a few experiments performed with the process and the preparations according to the present invention, are explained, for a better understanding of the invention itself.

(A) APPLICATION ONTO THE LEAVES

EXAMPLE 1

The experiment has been performed repeatedly with monomethyleneurea ($H_2NCON=CH_2$), or with monomethylolurea ($H_2NCONHCH_2OH$), or with dimethylene- or dimethylolurea, and the polymers thereof. The molecular reaction between urea and formaldehyde can be comprised within very wide limits, but the most convenient one (mainly if many sprayings must be effected) is comprised between the values of 1:0.80 and 1:0.95, i.e. leaving a percentage of molecules of non-combined urea comprised between 20% and 5%. The efficiency of the treatment depends mainly on the concentration of the formaldehyde put together with another monomer. Using pumps with a normal volume, the compound to be applied for each treatment must have a minimum concentration of 0.15 g/l (grams per liter), expressed in formaldehyde, and a maximum of 4 g/l if the used monomer is the urea. It should be noted that when phenol is used, the plants can bear doses also higher than twice as much. In the middle of August, and having only one or two sprayings, the maximum doses of 4 g/l can be applied; the only exceptions are plum trees and apricot trees, for which the doses must be halved. In springtime, in the case of slight parasitic attacks (cancers), usually two sprayings are sufficient at a distance of four-five days one from the other, said sprayings, effected with solutions of amino compounds which, expressed in formaldehydes, have a concentration of 3 g/l.

If, on the contrary, the areas of the bark attacked by the disease are large and widespread, it is necessary to continue the treatment, after two or three initial cures, repeating the treatment each ten-fifteen days, until an amelioration and finally complete recovery is obtained. For apricot trees and plum trees the dose must be reduced to at least 2 g/l. During two years, applications for totally 32 g have been effected onto peach trees and chestnut trees. The solutions of amino formaldehyde cause burns to the leaves, especially in the case of repeated treatments at a high concentration. Therefore, it is necessary to add buffer substances to said solution, said buffer substances consisting of organic acid salts, i.e. benzoates, citrates, acetates, of potassium, ammonium, hexamethylenetetramine and, eventually, in salts of formic acid and of methyl or ethyl alcohol.

The most commonly used solution of said salts, expressed in acids and in g/l, are the following:
  benzoic acid: 0.1÷0.2
  citric acid: 2÷2.5
  acetic acid: 0.5÷1.0
  hexamethylenetetramine: 0.6÷1.0
and eventually:
  formic acid: 0.2÷0.4
  methyl or ethyl alcohol: 0.5÷1.0

The content and the cationic relationship may vary within very large intervals, but not the anionic one. The pH must be adjusted in an interval comprised between 5.8 and 6.5. For the preparation of said solutions only technically pure elements have been employed, available on the market, and also common agricultural urea. However, it is also possible to work well with different pH's, opportunely choosing the buffers and nearly completely eliminating the cations except, obviously, for those contained in the water, using the excellent buffer solution consisting of:
  the anhydromethylencitrate of hexamethylenetetramine, $(HOOC-CH_2)_2-C-(OCO-CH_2O).C_6H_{12}N_4$: 2÷2.5 g/l
  tannic acid (tannin): 0.5÷1.0 g/l
  potassium formate: 0.2÷0.4 g/l
  formic acid: 0.2÷0.4 g/l
eventually adding:
  salicyclic acid: 0.1÷0.2 g/l The pH of said composition is 4.5. The use of buffers containing phthalic or phosphoric acid with the addition of agents blocking the calcium and magnesium ions is possible. Finally, a great part of said experimentation has been performed making urea to react with formaldehyde at a concentration from 1/10 to 1/20 of the final predetermined volume for spraying, and at a total pH comprised between 5 and 6, spraying successively, while the reaction was not yet completed.

The most advisable treatment period is the spring time (the vegetal stasis period should be avoided). The plant must be in the condition of forming new tissues and closing the wounds which requires, usually, a period comprised between twenty days and two months time. It should be further noted that the buffer's pH, or the pH of the spraying solution may vary considerably and may also be adjusted to the following considerations: an acid pH due to acid or acid salts, acts as a catalyst and therefore provokes a polymerization, making the reactions quicker and facilitating the recovery.

On the contrary, if the pH is near to neutrality, the leaves are protected, but the treatment is less active. The results noted after the application of said process are the following: the cancers of the bark, of fungal origin and of small dimensions, can all be cured, even if in great numbers. Those cancers which have attacked ⅛ to ¼ of the effective circumference of the branches have a great possibility of recovery: a recovery in the other cases is uncertain or impossible. Those cancers which are more easy to cure are the ones found on the trunk. The efficiency of the treatments according to the present invention is, however, subordinate to a good vegetative rankness, to the health and width of the foliage, and to the absence of other parasitic agents (Cochineal etc.). In the propitious cases a recovery of 80% of the cancers has been noted. No damage has been verified on the fruits of peach trees, of hard black cherry trees and of chestnut trees. On the leaves of the peach trees, on the contrary, due to the hanging position thereof, burning of the tops thereof has been noted when increasing the concentration of the active principle (formaldehyde) and of the number of treatments. Fungous attacks on the leaves or wounds, create the starting point for the development of burns, which burns are shown by the increase of holes or by the falling of the diseased leaves. For the peach trees, the noxious effects are not very important, because the tree is subject to a vegetative renewal. The apricot trees and the plum trees are much more sensitive, while the hard black cherry trees, the chestnut trees and the cherry trees are less sensitive.

EXAMPLE 2

The same formaldehyde compounds may be used, which have been mentioned before in example 1, or the methyl ethers of the methylolmelamines or of the methylolureas. It should however be noted that many syntheses of the methylolureas exist. One of said syntheses is here suggested because said synthesis appears to be the one which technically and commercially is the most appropriate as to avoid the presence of a great amount of uncondensed (non-combined) urea and formaldehyde.

Synthesis of mono- or dimethylolurea: 60 g of urea are added to 100 or 200 ml of an aqueous solution of formaldehyde at 30%, containing 25 ml of ammonia at 25%; the compound is heated in a water bath as to reach an average temperature of 40° C. in an hour, and not higher than—due to the exothermicity of the reaction—50° C.; the compound cools down to ambient temperature. When the mass has hardened, having assumed a caseous (cheese like) consistency, apparently lacking of water—which process requires at least 35 hours—the drying can be performed, by means of different methods but always at a low temperature, or the redissolution and dilution thereof can be performed also. It should be noted that the uncondensed materials, mainly non-combined formaldehyde, are the main cause for the burns on the leaves, so that the methylolureas, in the absence of the uncondensed material, do not require the addition of buffer substances to the spraying solution. On the contrary, if said compounds are used in the presence of uncondensed materials, the citrates are only necessary and sufficient as buffer substances, i.e. in doses starting from a minimum of 0.2 g/l to a maximum of 0.5 g/l of diammonium hydrogen citrate, together with tripotassium citrate (considered to be anhydrous) from a minimum of 1.3 g/l to a maximum of 3 g/l. The relationship in grams between the two salts is of 0.1:0.65. In any case, the final pH of the spraying solution must be very near to 6. But if the compound urea-formaldehyde does not exceed 2.5 g/l, it is not necessary to use buffers. However, the concentrations of urea-formaldehyde compounds, whichever it is, are comprised between 6 and 10 g/l for the initial treatment. If it is necessary to prosecute in the cure, the sprayings will be effected each seven-ten days with doses of 2 to 6 g/l. The small cancers and the pustules caused by "Coryneum" require one or two treatments; the medium cancers, which cover about ¼-1/5 of the circumference of the branch or trunk, require two or four sprayings, which may be augmented according to the dimension of the disease and if said disease has covered half the circumference of the branch or trunk, a complete recovery is improbable. Also the methyl ethers of the methylolureas and of the methylol melamines (the melamine is 2,4,6-triamino 1,3,5-triazine) can be used as curatives, as said substances can be better preserved and are well tolerated by the leaves. The concentrations in use must be reduced to 6 g/l for the initial treatments, if completely methylated compounds are used, such as e.g., di-ethers or hexa-ethers.

EXAMPLE 3

Another interesting compound thus obtained is: the ether of gallic acid ($C_6H_2COOH(OH)_3$) or the ether of di-gallic acid ($C_6H_2COO(OH)_3$—$C_6H_2KOOH(OH)_2$) with sugars having six atoms of carbon (or soluble hydrocarbons, esterified by aromatic acids containing hydroxyl (—OH); said substances react at an ambient temperature and up to 70° C. in the presence of formic acid (HCOOH) with the partial or total methyl ethers of methylolureas or methylolmelamines, or using methylolic compounds in the presence of methanol, or starting from solid urea and formaldehyde in solution, containing 20% of methanol. Before the reaction takes place, anhydromethylencitrate of hexamethylentetramine (($HOOC$—$CH_2)_2$—C—(OCO—$CH_2O$).$C_6H_{12}N_4$) or diammonium-hydrogen citrate and hexamethylentetramine in the molecular relationship of 1:1. The relationship in grams between the different reagents is the following:

1 g of ester
5 g of ether
0.2 g of formic acid
3 g of citrate.

The reaction can also be conducted at ambient temperature also with solutions at a concentration of 50 g/l of all the reagents and for some 10 minutes. At higher temperatures (40° C.) and at high concentrations, the reaction times are of only a few minutes. If the products of the reaction are not diluted and used for spraying, said products must be neutralized because otherwise the solution gets polymerized. The advantage of the substance thus obtained does not only consist in the fact of curing the cancers, but also in increasing the development of the chlorophyll, thus effecting a particularly intense green of the leaves, whereby said color can be mainly verified during the following springtime, if the sprayings have been effected in the middle of August.

(B) APPLICATION ONTO THE BARK: PREVENTIVE TREATMENT

A winter preventive cure (when the leaves have fallen down) onto the whole plant can be effected using the same already described compounds, particularly those ones for the cure, by spraying onto the leaves.

EXAMPLE 1

Preferably, the compounds hereinbelow described are the ones which are suggested for the cure by application onto the rind. The formaldehyde concentration can in this case be comprised between 1 and 5 g/l depending on the fact whether the formaldehyde is free or combined and according to the treatments (sprayings) which have to be effected each fifteen-thirty days:

(C) APPLICATION ONTO THE BARK

EXAMPLE 1

This cure is particularly referred to the cancer of the chestnut tree and is applied only to the diseased areas, i.e. to the cancers, and can be applied in any period of the year.

(a) for what concerns the less active cancers a single application onto the diseased part is sufficient, after the outer and peripheral coat of bark of the diseased areas has been removed. Said application is effected with preparations at a concentration of 4 to 7 g/l of compounds expressed in formaldehyde.

(b) the stronger cancers must be accurately and completely detected by carrying away only the outer coat of the bark. If the bark is very thin it is sufficient to remove the cuticle. It is preferred to delimit the periphery with a slight incision (⅓ of the rind) and then to paint the diseased area with doses of the compounds expressed in formaldehyde at a concentration from 7 to 40 g/l. Eventually, the painting will be repeated after one week.

One of the preparations which are easier to prepare and to use consists in:

paraformaldehyde $((-CH_2O-)_x)$: 5 g/l
non-combined formaldehyde: 25 g/l
eventually put together with
polyvinyl acetate: 30÷50 g/l.

The preparation acts against all the many manifestations of the disease: it is obviously only necessary that the plant is still alive. The springtime is the most favorable period for the treatment. No damage has been noted due to said preparations.

EXAMPLE 2

Other compositions have given the same effects, as for example the one resulting from amino-formaldehyde (with a simultaneous application of organic acids), phenol-formaldehyde (with or without addition of some g/l of hexamethylenetetramine) and with molecular relationships comprised between 1:1 and 1:2.5 and more.

The application processes described at point (C) example (1), are efficient also for the treatment of the bark of the gummy cancers of the Drupaceas; the peach trees, the apricot trees and the plum trees show the disadvantages of expelling "gum", and therefore it is preferred to effect the cure during the vegetative awakening.

The average of the recoverys, even if in different conditions and with widespread cancers, generally overcomes 80% of the cases, particularly if eventual active residua which were not comprised in the treatment, are always controlled.

From the studies and the experiments performed it resulted that the parasite from the wound, which is present in the bark of the different vegetal species, and which produces the greater damage, belongs to the same "Endothia parasitica".

Still keeping to the principle described as the basis of the present invention, it is understood that any variation can be applied to the compositions of the described examples, also for what concerns the application of said process to other species, without therefore going out of the limits of the present invention.

What I claim is:

1. A method of preventing or treating the diseases of bark cancer in chestnut trees and of gummosis in peach, apricot, plum, black cherry and cherry trees caused by fungi or bacteria, which method comprises applying to the bark or leaves of the trees by spraying or painting, an aqueous solution containing an amount effective against said fungi or bacteria of a formaldehyde reaction product selected from the group consisting of monomethyleneurea, dimethylene urea, monomethylolurea, dimethylolurea, dimethylol urea dimethyl ether, trimethylolmelamine trimethyl ether and hexamethylolmelamine hexamethyl ether.

2. The method according to claim 1, wherein the solution contains a buffer in an amount sufficient to obtain a pH of 4.5 to 6.5.

3. The method according to claim 2, wherein the buffer is selected from the group consisting of benzoates, citrates, acetates, phthalates, phosphates and tannic acid.

4. The method according to claim 3, wherein the citrate is the anhydromethylenecitrate of hexamethylenetetramine.

5. The method according to any one of claims 1–4, wherein the formaldehyde reaction product in the solution has a concentration of from 2 to 10 grams per liter.

6. A method of treating the disease of bark cancer in chestnut trees and of gummosis in peach, apricot, plum, black cherry and cherry trees caused by fungi or bacteria, which method comprises applying to the bark of the tree an aqueous solution of paraformaldehyde.

7. The method of treating the disease of bark cancer in chestnut trees according to claim 1 or 6, wherein the diseased area of the bark is treated with an aqueous solution having a concentration of 4 to 40 grams per liter calculated as formaldehyde.

8. The method according to claim 6, wherein the solution contains 5 grams per liter of paraformaldehyde, 25 grams per liter of uncombined formaldehyde and 30–50 grams per liter of polyvinyl acetate.

9. The method according to claim 1 or 6, wherein at least a portion of the bark adjacent to or including the diseased area is first removed prior to applying the aqueous solution thereto.

* * * * *